United States Patent [19]
Collier, IV et al.

[11] Patent Number: 5,169,706
[45] Date of Patent: Dec. 8, 1992

[54] LOW STRESS RELAXATION COMPOSITE ELASTIC MATERIAL

[75] Inventors: L. Warren Collier, IV, Alpharetta; Steven R. Stopper, Doraville, both of Ga.

[73] Assignee: Kimberly-Clark Corporation, Neenah, Wis.

[21] Appl. No.: 463,106

[22] Filed: Jan. 10, 1990

[51] Int. Cl.⁵ ............................................. B32B 27/14
[52] U.S. Cl. .................................... 428/152; 428/171; 428/172; 428/181; 428/182; 428/186; 428/198; 428/283; 428/284; 428/286; 428/287; 428/296; 428/297; 428/298; 428/326; 428/903
[58] Field of Search ............... 428/198, 152, 179, 181, 428/182, 186, 284, 903, 296, 287, 297, 298, 326, 283, 286, 171, 172

[56] References Cited
U.S. PATENT DOCUMENTS 4,892,903  1/1990  Himes .................................. 524/488

Primary Examiner—James J. Bell
Attorney, Agent, or Firm—Karl V. Sidor

[57] ABSTRACT

A composite elastic material having a stress relaxation of less than about 30 percent is composed of at least one elastic sheet formed from a blend of (1) a styrene-poly(ethylene-propylene)-styrene thermoplastic elastomeric block copolymer or a mixture of styrene-poly(ethylene-propylene)-styrene and styrene-poly(ethylene-butylene)-styrene elastomeric block copolymers, and (2) a tackifying resin. The blend may also include a polyolefin and/or an extending oil. The elastic sheet is joined to at least one gatherable layer at spaced-apart locations in which the gatherable layer is gathered between the spaced-apart locations so that the composite material is elastic.

32 Claims, 1 Drawing Sheet

LOW STRESS RELAXATION COMPOSITE ELASTIC MATERIAL

FIELD OF THE INVENTION

The present invention is generally directed to composite elastic materials and, in particular, to laminates of elastic and nonelastic materials.

BACKGROUND OF THE INVENTION

In the field of composite elastic materials, there has been a continuing need for composite materials having a high degree of flexibility and elasticity and which may be manufactured at a low cost. In particular, there is a need for a composite elastic material having low stress relaxation, low hysteresis and high recoverable energy. This need has persisted in spite of the fact that such materials could readily be utilized to manufacture a wide variety of garments of both the disposable type, such as disposable diapers, or the durable type, such as pants, dresses, blouses and sporting wear, for example, sweatsuits. Further, such materials could also be utilized in, for example, upholstery, drapery, liner and insulation applications. The characteristics of low stress relaxation, low hysteresis and high recoverable energy are particularly desirable for materials used in these areas because articles manufactured from such materials may be easily put on the body of the wearer or any item, such as a fixed frame, around which the materials may be wrapped. Those characteristics are also very useful because articles manufactured from such materials are able to closely conform to the body of a wearer or any item and repeatedly extend and retract without sagging.

Elastomeric block copolymers blended with large amounts of a polyolefin and/or hydrocarbon resin may, in certain situations, have poor stress relaxation properties and stress-strain tests of such materials show significant hysteresis. Moreover, elastic films or webs with the desired elastic properties may have those properties diminished when processed into a composite elastic material. For example, thermal bonding techniques used to join the elastic materials to the other materials of the composite or additives to the formulation of the elastic films or webs such as, for example tackifying resins which are utilized to enhance the bonding between the elastic materials and the other materials of the composite may have an adverse affect on the elastomeric properties of the elastic composite.

Thus, a void exists with respect to composite elastic materials which have the characteristics of low stress relaxation, low hysteresis and high recoverable energy.

DEFINITIONS

The term "elastic" is used herein to mean any material which, upon application of a biasing force, is stretchable, that is, elongatable at least about 60 percent (i.e., to a stretched, biased length which is at least about 160 percent of its relaxed unbiased length), and which, will recover at least 55 percent of its elongation upon release of the stretching, elongating force. A hypothetical example would be a one (1) inch sample of a material which is elongatable to at least 1.60 inches and which, upon being elongated to 1.60 inches and released, will recover to a length of not more than 1.27 inches. Many elastic materials may be elongated by much more than 60 percent (i.e., much more than 160 percent of their relaxed length), for example, elongated 100 percent or more, and many of these will recover to substantially their initial relaxed length, for example, to within 105 percent of their original relaxed length, upon release of the stretching force.

As used herein, the term "nonelastic" refers to any material which does not fall within the definition of "elastic," above.

As used herein, the terms "recover" and "recovery" refer to a contraction of a stretched material upon termination of a biasing force following stretching of the material by application of the biasing force. For example, if a material having a relaxed, unbiased length of one (1) inch is elongated 50 percent by stretching to a length of one and one half (1.5) inches the material would be elongated 50 percent (0.5 inch) and would have a stretched length that is 150 percent of its relaxed length. If this exemplary stretched material contracted, that is recovered to a length of one and one tenth (1.1) inches after release of the biasing and stretching force, the material would have recovered 80 percent (0.4 inch) of its one-half (0.5) inch elongation. Recovery may be expressed as [(maximum stretch length—final sample length)/(maximum stretch length—initial sample length)]×100.

The term "composite elastic material" as used herein refers to a multilayer material having at least one elastic layer joined to at least one gatherable layer at least at two locations in which the gatherable layer is gathered between the locations where it is joined to the elastic layer. A composite elastic material may be stretched to the extent that the nonelastic material gathered between the bond locations allows the elastic material to elongate. This type of composite elastic material is disclosed, for example, by U.S. Pat. No. 4,720,415 to Vander Wielen et al., issued Jan. 19, 1988, which is hereby incorporated by reference.

The term "stretch-to-stop" as used herein refers to a ratio determined from the difference between the unextended dimension of a composite elastic material and the maximum extended dimension of a composite elastic material upon the application of a specified tensioning force and dividing that difference by the unextended dimension of the composite elastic material. If the stretch-to-stop is expressed in percent, this ratio is multiplied by 100. For example, a composite elastic material having an unextended length of 5 inches and a maximum extended length of 10 inches upon applying a force of 2000 grams has a stretch-to-stop (at 2000 grams) of 100 percent. Stretch-to-stop may also be referred to as "maximum non-destructive elongation".

As used herein, the term "nonwoven web" means a web having a structure of individual fibers or threads which are interlaid, but not in an identifiable, repeating manner. Nonwoven webs have been, in the past, formed by a variety of processes such as, for example, meltblowing processes, spunbonding processes and bonded carded web processes.

As used herein, the term "microfibers" means small diameter fibers having an average diameter not greater than about 100 microns, for example, having an average diameter of from about 0.5 microns to about 50 microns, or more particularly, microfibers may have an average diameter of from about 4 microns to about 40 microns.

As used herein, the term "meltblown fibers" means fibers formed by extruding a molten thermoplastic material through a plurality of fine, usually circular, die capillaries as molten threads or filaments into a high velocity gas (e.g. air) stream which attenuates the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, the disclosure of which is hereby incorporated by reference.

As used herein, the term "spunbonded fibers" refers to small diameter fibers which are formed by extruding a molten thermoplastic material as filaments from a plurality of fine, usually circular, capillaries of a spinnerette with the diameter of the extruded filaments then being rapidly reduced as by, for example, eductive drawing or other well-known spun-bonding mechanisms. The production of spun-bonded nonwoven webs is illustrated in patents such as, for example, in U.S. Pat. No. 4,340,563 to Appel et al., and U.S. Pat. No. 3,692,618 to Dorschner et al. The disclosures of these patents are hereby incorporated by reference.

As used herein, the term "stress relaxation" refers to the loss of tension or load measured after a sample of an elastic material has been elongated at specified rate of extension to a predetermined length and held at that length for a specified period of time, for example, from about 1 minute to about 30 minutes. Except where otherwise noted for the present invention, stress relaxation is expressed as a percentage loss of the initial load encountered at a specified extension of an elastic material. The stress relaxation is determined by calculating the difference between the initial load measured after the elongation of an elastic material at a rate of 20 inches per minute to an elongation of 50 percent (i.e., to 150 percent of the material's initial length) and the remaining load measured after that sample was held at that length for 20 minutes divided by the initial load at that length. Testing may be performed on an Instron Model 1122 Universal Test Machine using a 100 mm by 3 inch sample attached to jaw faces that have a width of 3 inches and a height of 1 inch. Stress relaxation after 20 minutes at, for example, an elongation of 50% (i.e., to 150% of the material's initial length from 100 mm to 150 mm) may be expressed as a percentage utilizing the following equation:

stress relaxation = (peak load$_{50\%}$ − peak load50%@min)/(peak load$_{50\%}$)*100

As used herein, the term "average molecular weight" refers to the number average molecular weight of a polymer or polymer fragment as determined by gel permeation chromatography. Molecular weight information for styrene-poly(ethylene-propylene)-styrene elastomeric block copolymers and styrene-poly(ethylene-butylene)-styrene elastomeric block copolymers was obtained from the Shell Chemical Company.

As used herein, the term "polymer" generally includes, but is not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and random symmetries.

As used herein, the term "superabsorbent" refers to absorbent materials capable of absorbing at least 10 grams of aqueous liquid (e.g. distilled water per gram of and holding substantially all of the absorbed liquid while under a compression force of up to about 1.5 psi.

As used herein, the term "consisting essentially of" does not exclude the presence of additional materials which do not significantly affect the desired characteristics of a given composition or product. Exemplary materials of this sort would include, without limitation, pigments, antioxidants, stabilizers, surfactants, waxes, flow promoters, particulates and materials added to enhance processability of the composition.

As used herein, the term "compatible" refers to the relationship of one polymeric material to another with respect to the extrusion process and extrudates. To be compatible, two different polymeric materials should, for example, be capable of blending into a substantially homogeneous miscible mixture.

As used herein, the term "sheet" refers to a layer which may either be a film or a nonwoven web.

SUMMARY OF THE INVENTION

The present invention addresses problems of the prior art by providing a composite elastic material composed of: at least one elastomeric sheet formed from a blend including: (1) a styrene-poly(ethylene-propylene)-styrene elastomeric block copolymer or a mixture of styrene-poly(ethylene-propylene)-styrene and styrene-poly(ethylene-butylene)-styrene elastomeric block copolymers, and (2) a tackifying resin; and at least one gatherable layer, in which the elastic sheet and the gatherable layer are joined at spaced apart locations and the gatherable layer is gathered between the spaced-apart locations so that the composite material is elastic and has a stress relaxation of less than about 30 percent.

The styrene-poly(ethylene-propylene)-styrene thermoplastic elastomeric block copolymer component of the blend used to form the elastic sheet of the composite elastic material has a general formula of:

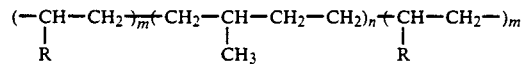

wherein m is an integer of at least about 38, for example, from about 38 to about 337; and n is an integer of at least about 500, for example, from about 500 to about 1860; and R is a benzyl group. The elastomeric block copolymer typically has an average molecular weight ranging from about 50,000 to about 90,000 and an average molecular weight ratio of polystyrene endblocks to poly(ethylene-propylene) midblocks ranging from about 10:90 to about 25:75. For example, one particularly useful elastomeric block copolymer has an average molecular weight of about 62,000 with polystyrene endblocks each having an average molecular weight of about 6200 and an average molecular weight ratio of polystyrene endblocks to poly(ethylene-propylene) midblocks of about 21.7:78.3.

In some situations, it may be desirable to blend the styrene-poly(ethylene-propylene)-styrene elastomeric block copolymer with another elastomeric block copolymer such as, for example, a styrene-poly(ethylene-butylene)-styrene block copolymer to form an elastomeric block copolymer mixture. Such a mixture may be used in place of a substantially pure styrene-poly(ethylene-propylene)-styrene elastomeric block copolymer and still achieve the desired stress-relaxation properties.

The tackifying resin component of the blend may be, for example, hydrogenated hydrocarbon resins and/or terpene hydrocarbon resins. The blend may further include a polyolefin and/or an extending oil. The polyolefin component of the blend may be selected from, for example, polyethylene, polypropylene, polybutylene, ethylene copolymers, propylene copolymers, butylene copolymers and mixtures thereof. The extending oil may be a mineral oil such as, for example, a white mineral oil.

The blend may contain from about 50 to about 80 percent, by weight, of the styrene-poly(ethylene-propylene)-styrene elastomeric block copolymer or a mixture of styrene-poly(ethylene-propylene)-styrene and styrene-poly(ethylene-butylene)-styrene elastomeric block copolymers, from about 15 to about 28 percent by weight of the tackifying resin, from about 3 to about 23 percent by weight of the polyolefin, and from about 0 to about 15 percent by weight of the extending oil.

The elastomeric sheet may be a nonwoven web of fibers such as, for example, a web of meltblown fibers or spunbonded fibers. The meltblown fibers may include microfibers. The elastic nonwoven web may also include at least one type of secondary fibers or particulate material.

The gatherable layer may be a film, such as, for example, a polypropylene film, or the gatherable layer may be a nonwoven web of fibers such as, for example, a web of spunbonded fibers, a web of meltblown fibers, a bonded carded web of fibers, or a multi-layer material including at least one of said webs of spunbonded fibers, meltblown fibers, or bonded carded web of fibers. The gatherable layer may also be a layer of pulp fibers including wood pulp fibers forming a material such as, for example, tissue.

The fibers of the gatherable layer may comprise a polymer selected from, for example, polyolefins, polyesters, and polyamides. The gatherable layer may also be a composite material containing a mixture of fibers and one or more other materials selected from the group consisting of wood pulp, staple fibers, particulates and super-absorbent materials, such as hydrocolloids.

DETAILED DESCRIPTION OF THE INVENTION

Figure 1:
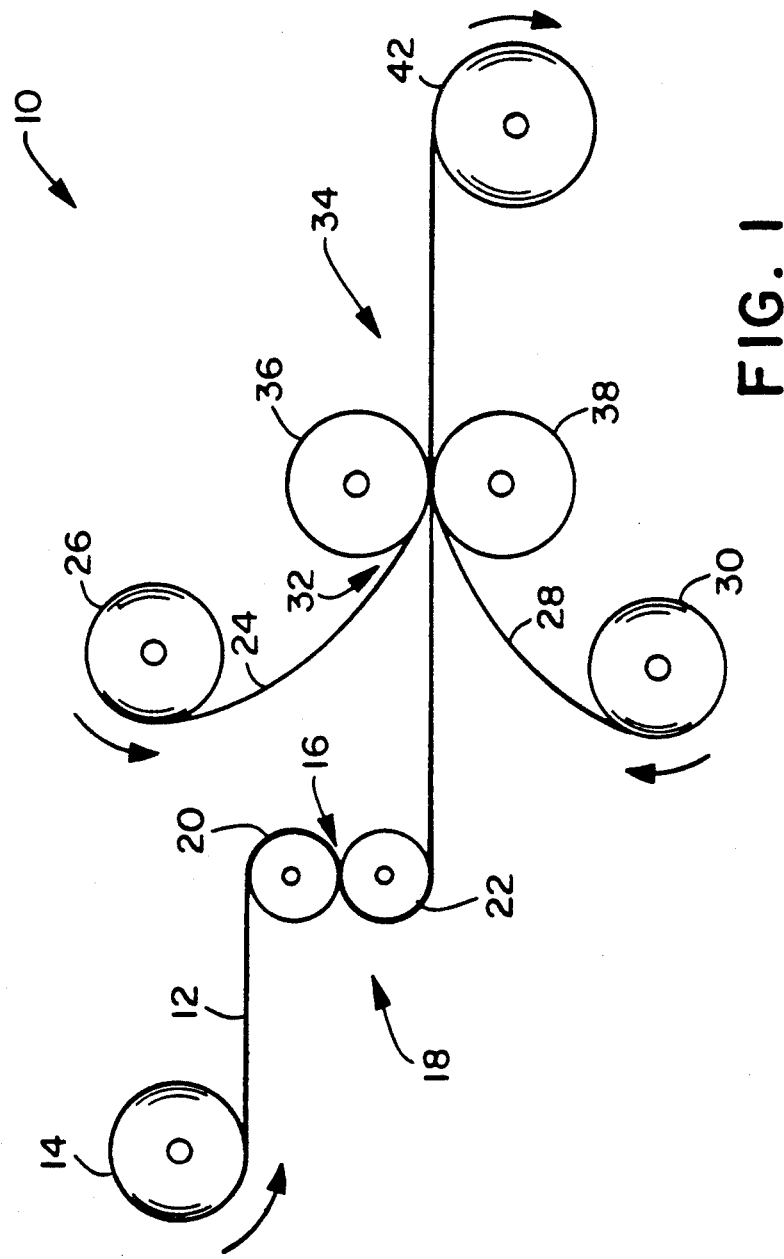
FIG. 1 is a schematic illustration of an exemplary process for forming a stretch-bonded laminate by laminating a gatherable web to each of the opposite sides of an elastomeric web.

Referring to FIG. 1 of the drawings there is schematically illustrated at 10 a process for forming a stretch-bonded laminate.

According to the present invention, an elastic sheet 12 is unwound from a supply roll 14 and travels in the direction indicated by the arrow associated therewith as the supply roll 14 rotates in the direction of the arrows associated therewith. The elastic sheet 12 passes through a nip 16 of the S-roll arrangement 18 formed by the stack rollers 20 and 22.

The elastic sheet 12 may also be formed by nonwoven extrusion processes, such as, for example, meltblowing processes or spunbonding processes, and passed directly through the nip 16 without first being stored on a supply roll.

A first gatherable layer 24 is unwound from a supply roll 26 and travels in the direction indicated by the arrow associated therewith as the supply roll 26 rotates in the direction of the arrows associated therewith. A second gatherable layer 28 is unwound from a second supply roll 30 and travels in the direction indicated by the arrow associated therewith as the supply roll 30 rotates in the direction of the arrows associated therewith.

The first gatherable layer 24 and second gatherable layer 28 pass through the nip 32 of the bonder roller arrangement 34 formed by the bonder rollers 36 and 38. The first gatherable layer 24 and/or the second gatherable layer 28 may be formed by extrusion processes such as, for example, meltblowing processes, spunbonding processes or film extrusion processes and passed directly through the nip 32 without first being stored on a supply roll.

The elastic sheet 12 passes through the nip 16 of the S-roll arrangement 18 in a reverse-S path as indicated by the rotation direction arrows associated with the stack rollers 20 and 22. From the S-roll arrangement 18, the elastic sheet 12 passes through the pressure nip 32 formed by a bonder roller arrangement 34. Additional S-roll arrangements (not shown) may be introduced between the S-roll arrangement and the bonder roller arrangement to stabilize the stretched material and to control the amount of stretching. Because the peripheral linear speed of the rollers of the S-roll arrangement 18 is controlled to be less than the peripheral linear speed of the rollers of the bonder roller arrangement 34, the elastic sheet 12 is tensioned between the S-roll arrangement 18 and the pressure nip of the bonder roll arrangement 32. By adjusting the difference in the speeds of the rollers, the elastic sheet 12 is tensioned so that it stretches a desired amount and is maintained in such stretched condition while the first gatherable layer 24 and second gatherable layer 28 is joined to the elastic sheet 12 during their passage through the bonder roller arrangement 34 to form a composite elastic material 40.

The composite elastic material 40 immediately relaxes upon release of the tensioning force provided by the S-roll arrangement 18 and the bonder roll arrangement 34, whereby the first gatherable layer 24 and the second gatherable layer 28 are gathered in the composite elastic material 40. The composite elastic material 40 is then wound up on a winder 42.

The gatherable layers 24 and 28 may be nonwoven materials such as, for example, spunbonded webs, meltblown webs, or bonded carded webs. If the gatherable layers 24 and 28 include a web of meltblown fibers, the meltblown fibers may include meltblown microfibers. The gatherable layers 24 and 28 may be made of fiber forming polymers such as, for example, polyolefins. Exemplary polyolefins include one or more of polypropylene, polyethylene, ethylene copolymers, propylene copolymers, and butylene copolymers. Useful polypropylenes include, for example, polypropylene available from the Himont Corporation under the trade designation PC-973, polypropylene available the Exxon Chemical Company under the trade designation Exxon 3445, and polypropylene available from the Shell Chemical Company under the trade designation DX 5A09.

In one embodiment of the present invention, one or both of the gatherable layers 24 and 28 is a multilayer material having, for example, at least one layer of spunbonded web joined to at least one layer of meltblown web, bonded carded web or other suitable material. For example, one or both of the gatherable layers 24 and 28 may be a multilayer material having a first layer of spunbonded polypropylene having a basis weight from about 0.2 to about 8 ounces per square yard (osy), a layer of meltblown polypropylene having a basis weight from about 0.2 to about 4 osy, and a second layer of spunbonded polypropylene having a basis weight of about 0.2 to about 8 osy. Alternatively, the one or both of the gatherable layers 24 and 28 may be single layer of material such as, for example, a spunbonded web having a basis weight of from about 0.2 to about 10 osy or a meltblown web having a basis weight of from about 0.2 to about 8 osy.

One or both of the gatherable layers 24 and 28 may also be a composite material made of a mixture of two or more different fibers or a mixture of fibers and particulates. Such mixtures may be formed by adding fibers and/or particulates to the gas stream in which meltblown fibers are carried so that an intimate entangled commingling of meltblown fibers and other materials, e.g., wood pulp, staple fibers and particulates such as, for example, hydrocolloid (hydrogel) particulates commonly referred to as superabsorbent materials, occurs prior to collection of the meltblown fibers upon a collecting device to form a coherent web of randomly dispersed meltblown fibers and other materials such as disclosed in U.S. Pat. No. 4,100,324, the disclosure of which is hereby incorporated by reference.

One or both of the gatherable layers 24 and 28 may be made of pulp fibers, including wood pulp fibers, to form a material such as, for example, a tissue layer. Additionally, the gatherable layers may be layers of hydraulically entangled fibers such as, for example, hydraulically entangled mixtures of wood pulp and staple fibers such as disclosed in U.S. Pat. No. 4,781,966, the disclosure of which is hereby incorporated by reference.

The elastic sheet 12 may also be a multilayer material in that it may include two or more individual coherent webs or films. Additionally, the elastic sheet 12 may be a multilayer material in which one or more of the layers contain a mixture of elastic and nonelastic fibers or particulates. An example of the latter type of elastic web, reference is made to U.S. Pat. No. 4,209,563, incorporated herein by reference, in which elastomeric and non-elastomeric fibers are commingled to form a single coherent web of randomly dispersed fibers. Another example of such a composite web would be one made by a technique such as disclosed, for example, in U.S. Pat. No. 4,741,949.

The gatherable layers 24 and 28 may be joined to the elastic sheet 12 at least at two places by any suitable means such as, for example, thermal bonding or ultrasonic welding which softens at least portions of at least one of the materials, usually the elastic sheet because the elastomeric materials used for forming the elastic sheet 12 have a lower softening point than the components of the gatherable layers 24 and 28. Joining may be produced by applying heat and/or pressure to the overlaid elastic sheet 12 and the gatherable layers 24 and 28 by heating these portions (or the overlaid layer) to at least the softening temperature of the material with the lowest softening temperature to form a reasonably strong and permanent bond between the re-solidified softened portions of the elastic sheet 12 and the gatherable layers 24 and 28.

The bonder roller arrangement 34 may be a smooth anvil roller 36 and a patterned calendar roller 38, such as, for example, a pin embossing roller arranged with a smooth anvil roller. One or both of the smooth anvil roller 36 and the calendar roller 38 may be heated and the pressure between these two rollers may be adjusted by well-known means to provide the desired temperature, if any, and bonding pressure to join the necked material 12 to the elastic sheet 32 forming a composite elastic necked-bonded material 40.

As can be appreciated, the bonding between the gatherable layers and the elastic sheet is a point bonding. Various bonding patterns can be used, depending upon the desired tactile properties of the final composite laminate material. When the gatherable layer is a material such as, for example, spunbonded polypropylene, such bonding can be performed at temperatures as low as 60° F. A range of temperatures for the calendar rolls during bonding between a gatherable layer such as, for example, spunbond polypropylene and an elastic sheet is 60° to 180° F., for example from 100° to 140° F., typically from about 110° to 125° F. In this regard, the bonding can be performed without heating the calendar rolls; however, without heating the calendar rolls there would be substantially no control of the temperature of the webs during bonding. Accordingly, it is desirable to heat the bonder (the calendar rolls) to a temperature in the range of 100° to 140° F. to control the temperature of the webs during bonding. As can be appreciated, in such temperature range (100° to 140° F.) bonding is provided by the tackiness of the elastic web (that is, the temperature is not so high as to cause softening of the elastic web and bonding primarily due to such softening). An advantage of the present invention is that due to the relatively low temperatures which can be used in the bonding step of the present invention, smaller distances between the bonding points can be used in the present invention, as compared with the distances used in conventional laminating techniques. Generally, the bonder rolls press against the laminate of webs such that the pressure between the rolls 36 and 38 at the pressure nip 32 is, for example, 100-500 pounds per linear inch (pli), typically about 250-350 pli. These pressures are about the same as utilized in conventional techniques to form composite elastic materials.

With regard to thermal bonding, one skilled in the art will appreciate that the temperature to which the materials, or at least the bond sites thereof, are heated for heat-bonding will depend not only on the temperature of the heated roll(s) or other heat sources but on the residence time of the materials on the heated surfaces, the compositions of the materials, the basis weights of the materials and their specific heats and thermal conductivities. However, for a given combination of materials, and in view of the herein contained disclosure the processing conditions necessary to achieve satisfactory bonding can be readily determined by one of skill in the art.

Conventional drive means and other conventional devices which may be utilized in conjunction with the apparatus of FIG. 1 are well known and, for purposes of clarity, have not been illustrated in the schematic view of FIG. 1.

As previously noted, the elastic sheet 12 is formed from a blend of: (1) a styrene-poly(ethylene-propylene)-styrene thermoplastic elastomeric block copolymer or a mixture of styrene-poly(ethylene-propylene)-styrene and styrene-poly(ethylene-butylene)-styrene elastomeric block copolymers, and (2) a tackifying resin. The blend may further include a polyolefin and an extending oil.

The styrene-poly(ethylene-propylene)-styrene thermoplastic elastomeric block copolymer component of the blend has a general formula of:

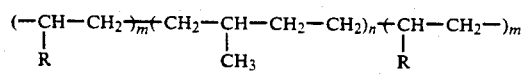

wherein m has a value of at least about 38, for example, from about 38 to about 337; and n has a value of at least about 500, for example, from about 500 to about 1860; and R is a benzyl group. Particularly useful values from range from about 48 to about 87 resulting in a polystyrene endblock having an average molecular weight from about 5,000 to about 10,000. Particularly useful values for n range from about 570 to about 1000 resulting in a poly(ethylene-propylene) midblock having an average molecular weight from about 40,000 to about 70,000. The total molecular weight of the polymer may be, for example, from about 50,000 to about 90,000. Such rubbery block copolymers may have an average molecular weight ratio of polystyrene endblocks to poly(ethylene-propylene) midblocks from about 10:90 to about 25:75. For example, one styrene-poly(ethylene-propylene)-styrene (SEPS) elastomeric block copolymer useful in the present invention is available from the Shell Chemical Company and has an average molecular weight of about 62,000 with polystyrene endblocks each having an average molecular weight of about 6200 and an average molecular weight ratio of polystyrene endblocks to poly(ethylene-propylene) midblocks of about 21.7:78.3. Exemplary properties of that SEPS polymer are given in Table 1.

TABLE 1

STYRENE-POLY(ETHYLENE-PROPYLENE)-STYRENE
BLOCK COPOLYMER
Physical Properties

| | |
|---|---|
| Tensile Strength[1], psi | 2260 |
| 300% Modulus[1], psi | 740 |
| Elongation at Break[1], % | 550 |
| Stress Relaxation[2], % | 23 |
| Hysteresis Properties[3]: | |
| Recoverable Energy[4], % | 77 |
| Set[5], % | 9 |

[1]Determined in accordance with ASTM D-412 using 3 mm wide (approximately 0.1 inch) and 0.020 inches thick dumbbell samples that were cut from films cast from toluene solution.
[2]Sample was elongated at 20 inches/minute to 160 percent elongation and held at 160 percent elongation for 30 minutes. Stress relaxation is the ratio determined by dividing the load after 30 minutes at 160 percent elongation by the peak load at 160 percent elongation and multiplying by 100.
[3]Hysteresis properties were measured by elongating the sample at 1 inch/minute to 150 percent elongation and cycling back to zero load for 1 hysteresis loop.
[4]Determined by dividing the area under the retraction curve of the first hysteresis loop by the area under the elongation curve of the first hysteresis loop and then multiplying by 100.
[5]Determined by dividing the zero load extension after 1 cycle by the initial sample gauge length and then multiplying by 100. The zero load extension is the distance that the jaws of the tensile test equipment moves at the beginning of the second cycle before a load is registered by the tensile test equipment.

In some situations, it may be desirable to blend the styrene-poly(ethylene-propylene)-styrene elastomeric block copolymer with another elastomeric block copolymer such as, for example, a styrene-poly(ethylene-butylene)-styrene block copolymer to form an elastomeric block copolymer mixture. Such a mixture may be used in the present invention in place of a substantially pure styrene-poly(ethylene-propylene)-styrene elastomeric block copolymer and still achieve the desired stress-relaxation properties. Useful elastomeric block copolymer mixtures may contain up to about 60 parts by weight of styrene-poly(ethylene-butylene)-styrene elastomeric block copolymer per 100 parts of elastomeric block copolymer and down to about 40 parts by weight of styrene-poly(ethylene-propylene)-styrene elastomeric block copolymer per 100 parts of elastomeric block copolymer. One useful styrene-poly(ethylene-butylene)-styrene elastomeric block copolymer has an average molecular weight of about 50,000 with polystyrene endblocks having an average molecular weight of about 7200 and an average molecular weight ratio of polystyrene endblocks to poly(ethylene-butylene) midblocks of about 30:70. Such a styrene-poly(ethylene-butylene)styrene block copolymer may be obtained from the Shell Chemical Company under the trade designation KRATON®G1652.

Various tackifying resins can be used in the present invention. In particular, the purpose of the tackifying resin is to provide an elastomeric web that can act as a pressure sensitive adhesive, e.g., to bond the elastomeric sheet to another web or layer of material. Of course, various tackifying resins are known, and are discussed, e.g., in previously mentioned Pat. No.4,789,699 and in previously mentioned U.S. Pat. Nos. 4,294,936 and 3,783,072, the contents of which, with respect to the tackifier resins, are incorporated herein by reference. Any tackifier resin can be used which is compatible with the elastomeric polymer and the polyolefin, and can withstand the high processing (e.g., extrusion) temperatures. Generally, hydrogenated hydrocarbon resins are preferred tackifying resins, because of their better temperature stability. The following paragraphs disclose information on three specific tackifying resins, two of which (REGALREZ® and ARKON®P series tackifiers) are examples of hydrogenated hydrocarbon resins, and the ZONATAC®501 lite being a terpene hydrocarbon. Of course, while the three tackifying resins are specifically discussed, the present invention is not limited to use of such three tackifying resins, and other tackifying resins which are compatible with the other components of the composition and can withstand the high processing temperatures, and can achieve the objectives of the present invention, can also be used.

REGALREZ® hydrocarbon resins, a product of Hercules, Incorporated, are fully hydrogenated α-methyl styrene-type low molecular weight hydrocarbon resins, produced by polymerization and hydrogenation of pure monomer hydrocarbon feed stocks. Grades 1094, 3102, 6108 and 1126 are highly stable, light-colored low molecular weight, nonpolar resins suggested for use in plastics modification, adhesives, coatings, sealants and caulks. The resins are compatible with a wide variety of oils, waxes, alkyds, plastics and elastomers and are soluble in common organic solvents.

ZONATAC® 501 lite resin, a product of Arizona Chemical Co., has a softening point of 105° C., a Gardner color 1963 (50% in heptane) of 1 — and a Gardener color neat (pure) of 2+ of 2+; a color (approximate Gardner color equal to 1 — (50% in heptane); APHA color =70) of water white, a specific gravity (25°/25° C.) of 1.02 and a flash point (closed cup, ° F.) of 480° F.

The polyolefin which may be utilized in the extrudable composition must be one which, when blended with the elastomeric block copolymer or mixture of elastomeric block copolymers and subjected to an appropriate combination of elevated pressure and elevated temperature conditions, is extrudable, in blended form, with the elastomeric block copolymer or mixture of elastomeric block copolymers. In particular, preferred polyolefin materials include polyethylene, polypropylene and polybutylene, including ethylene copolymers, propylene copolymers and butylene copolymers. Blends of two or more of the polyolefins may be utilized.

One particular polyethylene may be obtained from U.S.I. Chemical Company under the trade designation Petrothene NA601 (also referred to herein as PE NA601). Information obtained from U.S.I. Chemical Company states that PE NA601 is a low molecular weight, low density polyethylene for application in the area of hot melt adhesives and coatings. U.S.I. has also stated that PE NA601 has the following nominal values: (1) a Brookfield viscosity, cP at 150 degrees Centigrade of 8,500 and at 190 degrees Centigrade of 3,300 when measured in accordance with ASTM D 3236; (2) a density of 0.903 grams per cubic centimeter when measured in accordance with ASTM D 1505; (3) an equivalent Melt index of 2,000 grams per 10 minutes when measured in accordance with ASTM D 1238; (4) a ring and ball softening point of 102 degrees Centigrade when measured in accordance with ASTM E 28; (5) a tensile strength of 850 pounds per square inch when measured in accordance with ASTM D 638; (6) an elongation of 90% when measured in accordance with ASTM D 638; (7) a modulus of rigidity, $T_f(45,000)$ of $-34$ degrees Centigrade; and (8) a penetration hardness (tenths of mm) at 77 degrees Fahrenheit of 3.6.

Of course, the present invention is not limited to use of such specific polyolefins described herein. In this regard, note the polyolefins as described in U.S. Pat. Nos. 4,663,220 and 4,789,699, the contents of which are incorporated herein by reference. More generally, and noting the specific purpose of the polyolefin, as described in the U.S. Pat. application 4,663,220 of Tony J. Wisneski and Michael T. Morman, various polyolefins which can be utilized in the present invention can easily be determined.

Extending oils which may be used in the blend should be capable of being melt-processed with the other components of the blend without degrading. An exemplary extending oil is a white mineral oil available under the trade designation Drakeol 34 from the Pennzoil Company, Penreco Division. Drakeol 34 has a specific gravity of about 0.864 to about 0.878 at 60 degrees Fahrenheit, a flash point of about 460 degrees Fahrenheit, and a viscosity of about 370 to about 420 SUS at 100 degrees Fahrenheit. Suitable vegetable oils and animal oils or their derivatives may also be used as the extending oils.

The components of the blend used to form the elastic sheet can be utilized over broad ranges of the amounts of each component. As a guide, the best results have been obtained when utilizing a four component blend of a styrene-poly(ethylene-propylene)-styrene (SEPS) elastomeric block copolymer or mixture of styrene-poly(ethylene-propylene)-styrene (SEPS) elastomeric block copolymer and styrene-poly(ethylene-butylene)-styrene (SEBS) elastomeric block copolymer, a polyolefin, a tackifier, and an extending oil. The following ranges, as shown in Table 2, are exemplary. It is emphasized that these ranges are merely illustrative, serving as a guide for amounts of the various components in the composition.

TABLE 2

| | Weight % |
|---|---|
| SEPS elastomeric block copolymer or mixture of SEPS and SEBS elastomeric block copolymers | 50-80 |
| Tackifier | 15-28 |

TABLE 2-continued

| | Weight % |
|---|---|
| Polyolefin | 3-23 |
| Extending Oil | 0-15 |

As stated previously, while the extrudable elastomeric composition used to form the elastic sheet has been discussed in terms of a four-component extrudable composition of (1) styrene-poly(ethylene-propylene)-styrene elastomeric block copolymer or mixture of styrene-poly(ethylene-propylene)-styrene and styrene-poly(ethylene-butylene)-styrene elastomeric block copolymers; (2) polyolefin; (3) tackifying resin; and (4) extending oil; the polyolefin, which functions as a flow promoter for the composition can be substituted by other compatible flow promoters or processing aids, or can be eliminated altogether where the tackifying resin can also act as the flow promoter and/or extending oil. The extending oil, which functions as a processing aid, may also be substituted by other compatible processing aids or can be eliminated altogether where the tackifying resin can also act as the extending oil. For example, low molecular weight hydrocarbon resins such as REGALREZ ® can also act as the viscosity reducer and/or the extending oil, whereby the extrudable composition may contain the elastomeric block copolymer(s) and the tackifying resin (e.g., REGALREZ ®).

While the principal components of the blend used to form the elastic sheet have been described in the foregoing, such blend is not limited thereto, and can include other components not adversely affecting the blend attaining the stated objectives. Exemplary materials which could be used as additional components would include, without limitation, pigments, antioxidants, stabilizers, surfactants, waxes, flow promoters, solvents, particulates and materials added to enhance processability of the composition.

As indicated previously, the extrudable composition can be formed into a nonwoven web (e.g., a film, porous film or fibrous nonwoven web) by known extrusion techniques. A preferred extrusion technique is to form a fibrous elastic nonwoven web by meltblowing techniques.

Meltblowing processes generally involve extruding a thermoplastic polymer resin through a plurality of small diameter capillaries of a meltblowing die as molten threads into a heated gas stream (the primary air stream) which is flowing generally in the same direction as that of the extruded threads so that the extruded threads are attenuated, i.e., drawn or extended, to reduce their diameter to fiber or preferably microfiber size. The thus formed microfibers are then borne away from the vicinity of the die by the gas stream. The gas stream is directed onto a foraminous member, such as a screen belt or a screen drum which is moving over a vacuum box, so that the gas-borne fibers impinge upon and are collected on the surface of the foraminous member and form a cohesive fibrous nonwoven web. Meltblowing die arrangements usually extend across the foraminous collecting member in a direction which is substantially transverse to the direction of movement of the collecting surface. The die arrangements include a plurality of small diameter capillaries arranged linearly along the transverse extent of the die with the transverse extent of the die being approximately as long as the desired width of the fibrous nonwoven web which is to be produced. That is, the transverse dimension of the die is the dimension which is defined by the linear array of die capillaries. Typically, the diameter of the capillaries will be on the order of from about 0.01 inches to about 0.02 inches, for example, from about 0.0145 to about 0.018 inches. From about 5 to about 50 such capillaries will be provided per linear inch of die face. Typically, the length of the capillaries will be from about 0.05 inches to about 0.20 inches, for example, about 0.113 inches to about 0.14 inches long. A meltblowing die can extend for from about 20 inches to about 60 or more inches in length in the transverse direction.

Such meltblowing techniques, and apparatus therefore, are known in the art, and are discussed fully in U.S. Pat. No. 4,663,220, the contents of which have been previously incorporated herein by reference. For example, a blend containing, by weight, 57.7 percent styrene-poly(ethylene-propylene)-styrene elastomeric block copolymer (molecular weight 62,000) available from the Shell Chemical Company; 18.3 percent PE NA601; 18.2 percent REGALREZ® 1126; and 5.8 percent mineral oil was meltblown with the blend heated to a temperature of 480° F. Generally, and intended to be illustrative and not limiting, the following described parameters can be used for meltblowing the polymer blends to form the elastic nonwoven webs used in the composite elastic materials of the present invention. Thus, the blends can be meltblown while at a temperature of 450° to 550° F., preferably 475° to 500° F., during the meltblowing. The primary air temperature, during the meltblowing, can be 475° to 525° F., preferably 500° to 520° F.; and the primary air pressure can be 1.5–8 pounds per square inch (psi) gauge, preferably 2–4 psi gauge.

EXAMPLE 1

A blend containing, by weight, approximately 57.7% styrene-poly(ethylene-propylene)-styrene elastomeric block copolymer (molecular weight 62,000) available from the Shell Chemical Company; 18.3% PE NA601 polyethylene; 18.2% REGALREZ® 1126; and 5.8% Drakeol 34 was meltblown under the conditions of a melt temperature of 480° F.; a primary (forming) air temperature of 503° F. and a primary (forming) air pressure of 1.9 pounds per square inch (psi) gauge. The forming distance between the dies for the meltblowing and the forming wire was 14 inches. After formation of a meltblown web having a basis weight of approximately 50 gsm, the web was then passed directly to the stretch bond laminating process where two 0.4 osy webs of spunbonded polypropylene were joined to opposite sides of the elastic meltblown web. In this regard, attention is directed to FIG. 1. For such stretch bond laminating, the forming wire travelled at speed of 26 fpm, the S-roll arrangement traveled at a speed of 51 fpm, and the bonder rollers traveled at a speed of 141 fpm. The resulting composite elastic material had a stretch-to-stop of 180% and a draw ratio (i.e., bond roller speed/wire speed) of 5.42. The temperature of the bonder was 105° F., and the bonding pressure was 100 pounds per linear inch (pli).

EXAMPLES 2–5

Meltblown webs were formed from the same blend and under the same conditions as Example 1 except that the webs had basis weights of 65 gsm and 80 gsm. Two 0.4 webs of spunbonded polypropylene were joined to each side of the elastic web according to the process of Example 1 under the conditions given in the following Table 3:

TABLE 3

| Example | Basis Weight @ Wire (gsm) | Wire Speed (fpm) | S-Roll (fpm) | Calendar Speed (fpm) | Stretch to Stop | Cal/Wire Draw Ratio |
|---|---|---|---|---|---|---|
| 1 | 50 | 26 | 51 | 141 | 180% | 5.42 |
| 2 | 65 | 20 | 32 | 90.5 | 180% | 4.53 |
| 3 | 80 | 15 | 28 | 80 | 178% | 5.33 |
| 4 | 65 | 20 | 21 | 90 | 125% | 4.5 |
| 5 | 65 | 20 | 22 | 110 | 200% | 5.5 |

EXAMPLE 6

A blend containing, by weight, approximately 23.3% styrene-poly(ethylene-propylene)-styrene elastomeric block copolymer (molecular weight 62,000) available from the Shell Chemical Company; 35.0% styrene-poly(ethylene-propylene)-styrene elastomeric block copolymer available from the Shell Chemical Company under the trade designation KRATON® G-1652; 14.0% PE NA601 polyethylene; 18.4% REGALREZ® 1126 tackifying resin; and 9.3% Drakeol 34 mineral oil was meltblown under the conditions of a melt temperature of 480° F.; a primary (forming) air temperature of 498° F. and a primary (forming) air pressure of 1.9 psi (gauge). The forming distance between the meltblowing die tips and the forming wire was 14 inches. After formation of a meltblown web having a basis weight of approximately 50 gsm, the web was then passed directly to the stretch bond laminating process where two 0.4 osy webs of spunbonded polypropylene were joined to opposite sides of the elastic meltblown web. In this regard, attention is directed to FIG. 1. For such stretch bond laminating, the forming wire travelled at speed of 40 fpm, the S-roll arrangement traveled at a speed of 53 fpm, and the bonder rollers traveled at a speed of 240 fpm. The resulting composite elastic material had a stretch-to-stop of 180% and a draw ratio of 6.0 (i.e., bond roller speed/wire speed). The temperature of the bonder was 105° F., and the bonding pressure was 100 pli.

EXAMPLES 7–8

Using the same materials, equipment and procedures of Example 6, meltblown webs were formed having basis weights of approximately 65 gsm and 80 gsm. Each web was passed directly to the stretch bond laminating process where two 0.4 osy webs of spunbonded polypropylene were joined to opposite sides of each elastic meltblown web according to the procedure of Example 6. The resulting composite elastic materials each had a stretch-to-stop of approximately 180% and draw ratios of 5.31 and 4.65, respectively (i.e., bond roller speed/wire speed). The tensile properties of the composite elastic material formed from the elastomeric meltblown web having a basis weight of about 65 gsm is reported in Table 4 under the heading "Example 7". The tensile properties of the composite elastic material formed from the elastomeric meltblown web having a basis weight of about 80 gsm is reported in Table 4 under the heading "Example 8".

TENSILE TEST AND CYCLING DATA

The composite elastic materials of Examples 1–3 and 68 were tested to determine their tensile properties. The composite elastic materials were tested on a Constant Rate of Extension Tester, Instron Model 1122 Universal Testing Instrument. Three samples of each material were cut to 3" width by 7" length, with the 7" dimension running along the machine direction of the material (i.e., in the direction of stretch measurement). The samples were cut along the same machine direction position for sample uniformity Each sample was placed lengthwise in jaw faces having a width of 3 inches and a height of 1 inch, with a jaw span or separation of 100 mm. The Instron crosshead speed was set at 20 inches per minute.

The stretch-to-stop or maximum elongation under a 2000 gram tensioning force was determined for each sample. The composite elastic material was cycled twice to a 125% elongation (i.e., 225 mm final length) and measurements were taken of the peak load at 50% elongation. The tension during the unload portion of the second cycle was measured at 75% elongation.

The composite elastic material was held at 50% elongation and the load was measured immediately, then after 1 minute and after 20 minutes. A value for the stress relaxation was determined from the difference between the initial load at 50% elongation and the load after 20 minutes at 50% elongation divided by the initial load at 50% elongation (multiplied by 100 percent). The basis weight of the elastic nonwoven web in the composite elastic material sample was determined by weighing the elastic web after delaminating the composite elastic material sample. Isopropyl alcohol was used to soak the sample until the gatherable layer could easily be peeled from the elastic sheet. The elastic material was clipped to a drying line under a fume hood and allowed to dry for about 5 minutes before the sample was removed from the drying line and weighed.

As can been seen from Table 4, the elongation and load values may be varied over a wide range by varying the process conditions used to form the composite elastic material. For example, changing the basis weight will affect the load or the draw ratio will affect the load and stretch-to-stop (See Examples 1-3 and 6-8). The values reported in Table 4 are average values for 2 replicate tests.

TABLE 4

| | Example No. | | | | | |
|---|---|---|---|---|---|---|
| Basis Weight On Wire (gsm) | 1 50 | 2 65 | 3 80 | 6 50 | 7 65 | 8 80 |
| PEAK Load[1] @ 50% elongation | 385.8 | 436.8 | 899.8 | 268.6 | 376.2 | 418.4 |
| 1 MIN. Load[1] @ 50% elongation | 324.4 | 371.4 | 776.3 | 225.6 | 314.8 | 351.5 |
| 20 MIN. Load[1] @ 50% elongation | 286.1 | 325.2 | 701.4 | 197.7 | 272.6 | 306.1 |
| Stress Relaxation[2] | 25.8 | 25.2 | 22.0 | 26.4 | 27.0 | 27.0 |
| Basis Weight[3] of elastic in SBL | 70.7 | 93.9 | 185.0 | 51.7 | 60.3 | 74.1 |
| 2$^{nd}$ Cycle Unload[1] at 75% elongation | 325.7 | N.A. | 795.6 | 232.2 | 286.4 | 329.6 |
| 1 MIN. Load/ Basis Weight Ratio | 4.6 | 4.0 | 4.2 | 4.4 | 5.2 | 4.7 |
| 2$^{nd}$ Cycle Unload/Basis Weight Ratio | 4.6 | N.A. | 4.3 | 4.5 | 4.7 | 4.4 |
| Stretch-to-Stop[2] (maximum elongation) | 180 | 158 | 144 | 145 | 116 | 108 |

TABLE 4-continued

| | Example No. | | | | | |
|---|---|---|---|---|---|---|
| Basis Weight On Wire (gsm) | 1 50 | 2 65 | 3 80 | 6 50 | 7 65 | 8 80 |

[1]grams force
[2]Percent
[3]Grams per square meter

RELATED APPLICATIONS

This application is one of a group of patent applications which are being filed on the same date. The group includes the present application and application Serial No. 07/463,079 in the name of S. R. Stopper et al., and entitled "Low Stress Relaxation Elastomeric Nonwoven Webs and Fibers". The subject matter of that patent application is hereby incorporated by reference.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A composite elastic material having a stress relaxation of less than about 30 percent comprising:
    at least one elastic sheet formed from a blend comprising:
        an elastomeric polymer selected from the group consisting of styrene-poly(ethylene-propylene)-styrene elastomeric block copolymer and a mixture of styrene-poly(ethylene-polypropylene)-styrene and styrene-poly(ethylene-butylene)-styrene elastomeric block copolymers; and a tackifying resin; and
    at least one gatherable layer joined at spaced apart locations to the elastic sheet, and
    wherein the gatherable layer is gathered between the spaced-apart locations.

2. The composite elastic material of claim 1, wherein the styrene-poly(ethylene-propylene)-styrene thermoplastic elastomeric block copolymer has the formula:

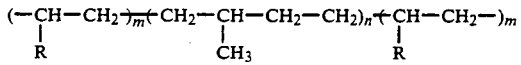

wherein m is an integer from about 38 to 337; and n is an integer from about 500 to 1860; and R is a benzyl group.

3. The composite elastic material of claim 2, wherein the styrene-poly(ethylene-propylene)-styrene elastomeric block copolymer has an average molecular weight ratio of polystyrene endblocks to poly(ethylene-propylene) midblocks ranging from about 10:90 to about 25:75.

4. The composite elastic material of claim 1 wherein the elastic sheet formed from a blend comprising a mixture of styrene-poly(ethylene-prolpropylene)-styrene and styrene-poly(ethylene-butylene)-styrene elastomeric block copolymers contains at least about 40 parts by weight styrene-poly(ethylene-polypropylene)-styrene elastomric block copolymer per 100 parts of elastomeric block copolymer.

5. The composite elastic material of claim 1, wherein the tackifying resin is selected from the group including hydrogenated hydrocarbon resins and terpene hydrocarbon resins.

6. The composite elastic material of claim 1, wherein the elastic sheet is formed from a blend further comprising a polyolefin resin.

7. The composite elastic material of claim 6, wherein the polyolefin resin is selected from the group including polyethylene, polypropylene, polybutylene, ethylene copolymers, propylene copolymers, butylene copolymers and mixtures thereof.

8. The composite elastic material of claim 6, wherein the blend further includes an extending oil.

9. The composite elastic material of claim 8, wherein the blend comprises from about 50 to about 80 percent, by weight, of an elastomeric polymer, from about 15 to about 30 percent, by weight, of a tackifying resin, from about 3 to about 25 percent, by weight, of a polyolefin, and from about 0 to about 15 percent, by weight, of an extending oil.

10. The composite elastic material of claim 1, wherein the elastic sheet is an elastic nonwoven web of meltblown fibers.

11. The composite elastic material of claim 10, wherein the web of meltblown fibers includes microfibers.

12. The composite elastic material of claim 1 wherein the gatherable layer is a nonwoven web of fibers.

13. The composite elastic material of claim 12 wherein the gatherable layer is selected from the group consisting of a web of spunbonded fibers, a web of meltblown fibers, a bonded carded web of fibers, a multi-layer material including at least one of the webs of spunbonded fibers, meltblown fibers, and a bonded carded web of fibers.

14. The composite elastic material of claim 12, wherein the gatherable layer comprises a nonwoven web of fibers formed from a polymer selected from the group consisting of polyolefins, polyesters, and polyamides.

15. The composite elastic material of claim 14, wherein the nonwoven web of fibers is formed from a polyolefin selected from the group consisting of one or more of polyethylene, polypropylene, polybutylene, ethylene copolymers, propylene copolymers, and butylene copolymers.

16. The composite elastic material of claim 12, wherein the gatherable layer is a nonwoven web comprising a mixture of fibers and one or more other materials selected from the group consisting of wood pulp, staple fibers, particulates and super-absorbent materials.

17. A composite elastic material having a stress relaxation of less than about 30 percent comprising:
at least one elastic sheet formed from a blend comprising:
an elastomeric polymer selected from the group consisting of styrene-poly(ethylene-propylene)-styrene elastomeric block copolymer and a mixture of styrene-poly(ethylene-polypropylene)-styrene and styrene-poly(ethylene-butylene)-styrene elastomeric block copolymers; a polyolefin; a tackifying resin; and an extending oil, and
at least one gatherable layer joined to the elastic sheet at spaced apart locations, and
wherein the gatherable layer is gathered between the spaced-apart locations.

18. The composite elastic material of claim 17, wherein the styrene-poly(ethylene-propylene)-styrene elastomeric block copolymer has the formula:

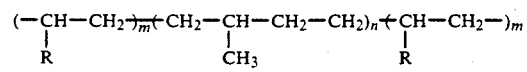

wherein m is an integer from about 38 to 337; and n is an integer from about 500 to 1860; and R is a benzyl group.

19. The composite elastic material of claim 18, wherein the styrene-poly(ethylene-propylene)-styrene elastomeric block copolymer has an average molecular weight ratio of polystyrene endblocks to poly(ethylene-propylene) midblocks ranging from about 10:90 to about 25:75.

20. The elastic nonwoven web of claim 17 wherein the mixture of styrene-poly(ethylene-polypropylene)-styrene and styrene-poly(ethylene-butylene)-styrene elastomeric block copolymers contains at least about 40 parts by weight styrene-poly(ethylene-polypropylene)-styrene elastomeric block copolymer per 100 parts of elastomeric block copolymer.

21. The composite elastic material of claim 17, wherein the polyolefin is selected from the group including polyethylene, polypropylene, polybutylene, ethylene copolymers, propylene copolymers, butylene copolymers and mixtures thereof.

22. The composite elastic material of claim 17, wherein the tackifying resin is selected from the group including hydrogenated hydrocarbon resins and terpene hydrocarbon resins.

23. The composite elastomeric material of claim 17, wherein the extending oil is mineral oil.

24. The composite elastic material of claim 17, wherein the blend comprises from about 0 to about 80 percent, by weight, of an elastomeric polymer, from about 15 to about 30 percent, by weight, of a tackifying resin, from about 3 to about 25 percent, by weight, of a polyolefin, and from about 0 to about 15 percent, by weight, of an extending oil.

25. The composite elastic material of claim 17, wherein the elastic sheet is an elastic nonwoven web of meltblown fibers.

26. The composite elastic material of claim 25, wherein the meltblown fibers include microfibers.

27. The composite elastic material of claim 17, wherein the gatherable layer is a nonwoven web of fibers.

28. The composite elastic material of claim 27, wherein the gatherable layer is selected from the group consisting of a web of spunbonded fibers, a web of meltblown fibers, a bonded carded web of fibers, a multi-layer material including at least one of the webs of spunbonded fibers, meltblown fibers, and bonded carded web of fibers.

29. The composite elastic material of claim 28, wherein the meltblown web of fibers includes microfibers.

30. The composite elastic material of claim 27, wherein the gatherable layer comprises a nonwoven web of fibers formed from a polymer selected from the group consisting of polylofens, polyesters, and polyamides.

31. The composite elastic material of claim 30, wherein the gatherable later comprises a nonwoven web of fibers formed from a polyolefin selected from the group consisting of one or more of polyethylene, polypropylene, polybutylene, ethylene copolymers, propylene copolymers, and butylene copolymers.

32. The composite elastic material of claim 17, wherein the gatherable layer is a nonwoven web comprising a mixture of fibers and one or more other materials selected from the group consisting of wood pulp, staple fibers, particulates and super-absorbent materials.

* * * * *